(12) United States Patent
Margairaz et al.

(10) Patent No.: US 8,431,855 B2
(45) Date of Patent: Apr. 30, 2013

(54) METHOD OF MAKING A METAL BELLOWS ASSEMBLY HAVING AN INTERMEDIATE PLATE

(75) Inventors: Philippe Margairaz, Newton, MA (US); Pierre Pringalle, Montmollin (CH); Jean-Sebastien Petithory, LaChaux de Fonds (CH)

(73) Assignee: Codman Neuro Sciences Sarl (CH)

( * ) Notice: Subject to any disclaimer, the term of this patent is extended or adjusted under 35 U.S.C. 154(b) by 1056 days.

(21) Appl. No.: 12/251,958

(22) Filed: Oct. 15, 2008

(65) Prior Publication Data
US 2009/0188897 A1  Jul. 30, 2009

Related U.S. Application Data

(63) Continuation-in-part of application No. 11/552,343, filed on Oct. 24, 2006, now Pat. No. 7,905, 878.

(60) Provisional application No. 60/731,678, filed on Oct. 31, 2005.

(51) Int. Cl.
*B23K 35/38* (2006.01)

(52) U.S. Cl.
USPC .................. 219/75; 219/121.63; 219/121.64; 29/454

(58) Field of Classification Search .................... 219/75, 219/121.63, 121.64, 137 R; 92/34–47; 29/428, 29/454
See application file for complete search history.

(56) References Cited

U.S. PATENT DOCUMENTS

| 1,717,196 | A | * | 6/1929 | Emmet | 92/45 |
| 2,071,583 | A | * | 2/1937 | Schutt | 228/137 |
| 2,534,123 | A | * | 12/1950 | Hasselhorn | 148/529 |

(Continued)

OTHER PUBLICATIONS

U.S. Appl. No. 11/552,343, Non-Final Rejection dated Feb. 19, 2010.

(Continued)

*Primary Examiner* — Henry Yuen
*Assistant Examiner* — John Wasaff

(57) ABSTRACT

The formation of a bellows made up of a stack of a predetermined number of ring-convolutions and having an intermediate plate supported within said stack is achieved by supplying several thin metal rings, each having inner and outer edges. A pair of these metal rings are positioned in contiguous relationship and their adjacent inside edges are welded together to form a ring-convolution. This process is repeated until a sufficient number of ring-convolutions are made to eventually make the desired bellows. Before these separate ring-convolutions are fused to each other, an intermediate plate and a support ring are made. The intermediate plate is a disc of metal that is sized smaller than the inside diameter of the rings and is secured to the support ring. The support ring is then positioned between two formed ring-convolutions in contiguous relationship and the three abutting outside edges are welded to each other to form a support plate convolution. The already made ring-convolutions and the support plate convolution are then stacked in the desired order and in contiguous relationship. All not-yet welded adjacent outside edges of said ring-convolutions and said support plate convolution are then welded to form the bellows. A bottom plate is formed and welded to the outside edge of the bottommost ring-convolution and a top ring is finally welded to the uppermost convolution to complete the bellows. The top ring is meant to be welded to a base plate of an infusion pump.

36 Claims, 6 Drawing Sheets

U.S. PATENT DOCUMENTS

| | | | | |
|---|---|---|---|---|
| 2,534,124 A | * | 12/1950 | Hasselhorn | 148/518 |
| 2,657,075 A | * | 10/1953 | Schwester et al. | 138/121 |
| 2,771,095 A | * | 11/1956 | Peters | 92/45 |
| 2,811,173 A | * | 10/1957 | Benson | 92/45 |
| 2,925,829 A | * | 2/1960 | Thompson, Sr. | 92/45 |
| 3,284,264 A | * | 11/1966 | O'Rourke | 156/289 |
| 3,731,681 A | | 5/1973 | Blackshear | |
| 3,831,499 A | | 8/1974 | Andrews | |
| 3,918,622 A | * | 11/1975 | Larsen | 228/8 |
| 4,360,019 A | | 11/1982 | Portner | |
| 4,457,213 A | * | 7/1984 | Morgan | 92/42 |
| 4,496,097 A | * | 1/1985 | Larsen | 228/212 |
| 4,500,026 A | * | 2/1985 | Larsen | 219/137 R |
| 4,505,710 A | | 3/1985 | Collins | |
| 4,525,165 A | | 6/1985 | Fischell | |
| 4,760,236 A | * | 7/1988 | Stoll | 219/121.63 |
| 4,781,680 A | | 11/1988 | Redmond et al. | |
| 4,910,642 A | | 3/1990 | Downing | |
| 5,137,529 A | | 8/1992 | Watson et al. | |
| 5,261,317 A | * | 11/1993 | Fraser, Jr. | 92/42 |
| 5,410,123 A | * | 4/1995 | Rancourt | 219/121.63 |
| 5,507,737 A | | 4/1996 | Palmskog | |
| 5,607,418 A | | 3/1997 | Arzbaecher | |
| 5,667,504 A | | 9/1997 | Baumann | |
| 5,954,687 A | | 9/1999 | Baudino | |
| 6,040,550 A | | 3/2000 | Chang | |
| 6,078,021 A | | 6/2000 | Chang | |
| 6,380,510 B1 | * | 4/2002 | Chang | 219/121.63 |
| 6,482,177 B1 | | 11/2002 | Leinders | |
| 6,755,814 B2 | | 6/2004 | Wieland et al. | |
| 6,818,857 B1 | * | 11/2004 | Cho et al. | 219/121.64 |
| 6,852,106 B2 | | 2/2005 | Watson et al. | |
| 7,725,272 B2 | | 5/2010 | Ginggen | |
| 2002/0138068 A1 | | 9/2002 | Watson et al. | |
| 2003/0120262 A1 | | 6/2003 | Wieland | |
| 2003/0226247 A1 | | 12/2003 | Williamson | |
| 2007/0106280 A1 | | 5/2007 | Utard | |

OTHER PUBLICATIONS

U.S. Appl. No. 11/552,343, Final Rejection dated Aug. 4, 2010.

\* cited by examiner

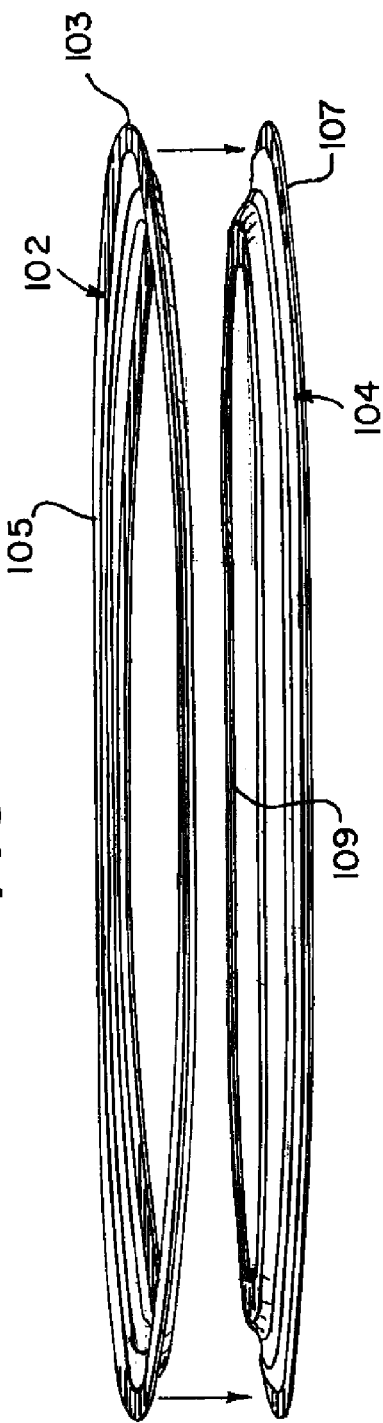
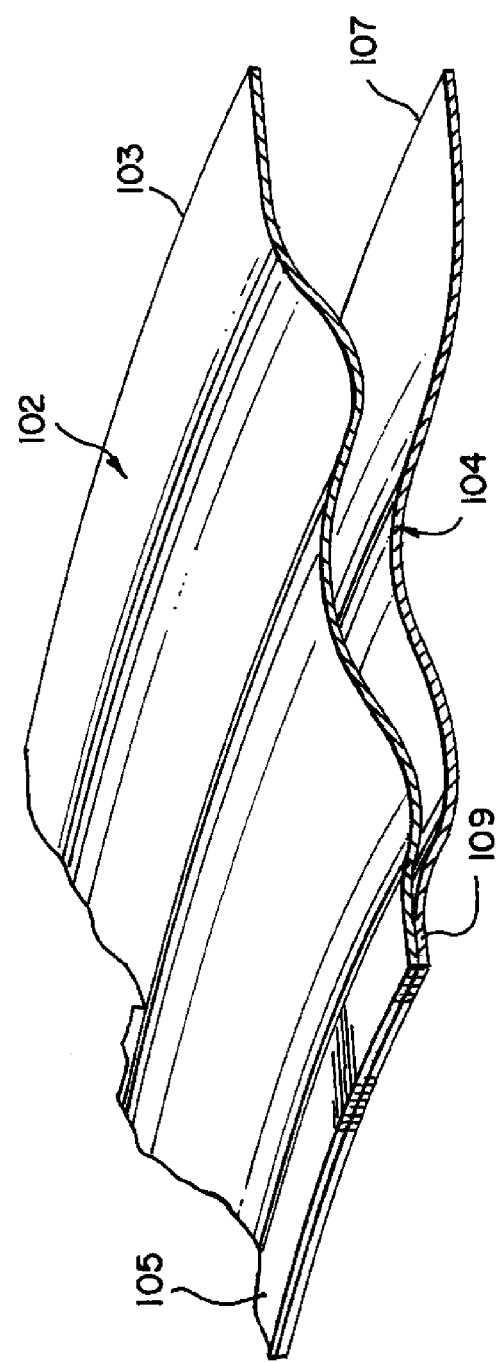

METHOD OF MAKING A METAL BELLOWS ASSEMBLY HAVING AN INTERMEDIATE PLATE

RELATED APPLICATIONS

This application is a continuation-in-part of US Provisional Patent Application No. 60/731,678 filed on Oct. 31, 2005, entitled "Implantable Pump with Reservoir with Level Detector", and US Non-Provisional patent application Ser. No. 11/552,343 filed on Oct. 24, 2006, entitled "Implantable Pump with Reservoir Level Detector", the disclosures of which are hereby incorporated by reference in their entirety.

BACKGROUND OF THE INVENTION

1) Field of the Invention

The present invention generally relates to the method of manufacture of metal bellows of the type used to form a fluid reservoir in implantable infusion pumps, and more particularly, to the method of manufacture of such metal bellows having an intermediate plate to aid in accurate sensing of the volume of the bellows.

2) Discussion of Related Art:

Extremely thin-gauge titanium welded bellows are commonly used in implantable infusion pumping devices as the main drug reservoir. A pump of this type is implanted within a patient and is used to accurately administer a precise dose of a stored liquid medication either continuously or at carefully timed intervals. As is well known in the art, within these small pumps, a metal bellows holds a supply of a liquid medication and is located within a sealed rigid propellant chamber containing a pressurized gas. The surrounding pressure differential within the chamber applies an even force to the bellows, which in turn collapses against the liquid medication within in a controlled and predictable manner. The collapsing bellows applies an even force to the contained liquid medication and in doing so, forces the liquid through controlling conduits and valves located elsewhere within the pump, eventually expelling the liquid medication to a target site within the patient. The liquid typically passes through what is called a micro-channel restrictor so that even though the pressure exerted on the liquid medication is very high, it dispenses from the pump at an extremely slow and controlled rate.

Since these pumps are surgically implanted within a patient, they are for the most part, inaccessible for long periods of time. For this reason, electrical and magnetic signals are typically used as a means of communication between the different sensing and controlling systems within the pump and remote monitoring devices located outside the patient's body. One such sensing system is used to detect the amount of medicament remaining the fluid reservoir of the pump. For obvious health reasons, it is important to know the moment the medicament level falls to a predetermined threshold so that the patient is never without treatment, as prescribed. When the threshold is reached, a piercing conduit can be used to replenish the liquid medicament supply within the bellows by penetrating the patient's skin and an additional septum within the pump.

Although there are likely different sensing methods that could be used to determine the amount of medicament within the fluid reservoir of these implantable pumps, one preferred system is disclosed in U.S. Pat. No. 6,755,814, which is commonly owned by the assignee of the present invention.

U.S. Pat. No. 6,755,814 discloses an implantable infusion pump that has a reservoir level detector. The pump includes a housing having a base plate which separates the housing into a pump electronic chamber and a propellant chamber. A bellows mechanism is disposed within the propellant chamber. The bellows mechanism has a bottom plate and defines a collapsible fluid reservoir into which the medicament for delivery to a patient is stored. A propellant is disposed about the bellows mechanism within the propellant chamber. The propellant compresses the bellows mechanism and thereby pushes the medicament out of the bellows mechanism through a flow restrictor, a valve and an outlet of the pump. As the bellows empties, the bottom plate naturally advances towards the base plate of the pump.

According to U.S. Pat. No. 6,755,814, a sensing circuit including a capacitor and a coil disposed within the base plate is used to form a resonant circuit. When energized, the coil generates a primary electromagnetic field, which flows through the bottom plate of the bellows mechanism and induces eddy currents therein. The strength of these eddy currents increases as the bottom plate moves closer to the coil within the base place. The eddy currents generate a secondary magnetic field, which is coupled back to the primary field. The closer the bottom plate is to the coil, the stronger the secondary magnetic field is and its influence on the primary field. This flux coupling brings about change to the inductance of the coil and thus brings about a displacement or shift of the resonance frequency of the resonant circuit depending on the distance between the coil and the bottom plate. Upon measuring the resonance frequency, which is dependent upon the inductance, well known circuitry can be employed to calculate the distance that the bottom plate of the bellows mechanism is from the base plate. This distance can then be used to determine the effective volume of the fluid reservoir and also the amount of medicament remaining within the bellow mechanism. An appropriate circuit can use this information to selectively create an alarm signal in response to a predetermined resonant frequency being reached.

In the prior art, such as the apparatus disclosed in U.S. Pat. No. 6,755,814, the measurement of fluid remaining in the reservoir is only accurate for the last 20 ml of fluid within the bellows mechanism. At fluid levels greater than about 20 ml and because of the increasing distance between the coil and the bottom plate at those greater volumes, the measured inductance doesn't vary sufficiently to provide accurate measurements.

In an effort to solve this problem, Applicant has filed US Patent Application No 2007/0106280 on Oct. 24, 1006, based on a provisional case filed Oct. 31, 2005, which is also commonly owned by the assignee of the present invention. U.S. Patent Application No. 2007/0106280 discloses an implantable infusion pump having the same main parts and operating in basically the same manner as that described above in U.S. Pat. No. 6,755,814, but further including an "intermediate plate". This intermediate plate is secured within the bellows structure and inside the fluid reservoir and works with the resonant sensing circuit so that the volume of fluid within the bellows mechanism can be measured with a greater degree of accuracy, not only above 20 ml, but also within the critical range of between 0 and 20 ml.

To help explain the present invention, a quick discussion of the basic structure and operation of the pump of US Patent Application No 2007/0106280 is in order. To this end, referring now to FIG. 1 of the present application, an implantable pump 10 in accordance with the invention disclosed in U.S. Patent Application No 2007/0106280 is shown. Pump 10 has a housing 12. The housing is comprised of a base plate 14 and a can 13. Can 13 is attached to the base plate 14. Base plate 14 divides the housing into an electronics chamber 16 and a propellant chamber 18. A bellows mechanism 20 is connected to the base plate 14 and is disposed within the propellant chamber 18. The bellows mechanism 20 has a hermetically sealed expandable sidewall 22 and a bottom plate 24. The bellows mechanism 20 divides the propellant chamber into a medicament-receiving portion 26 and a non-medicament receiving portion 28. In one preferred exemplary embodiment of U.S. Patent Application No. 2007/0106280 a propellant located within propellant-receiving portion 28 applies an even force the adjacent bellows 20 causing the medicament within medicament-receiving portion 26 to be delivered to an outlet of pump 10 in a manner known to those skilled in the art. Alternatively, the pump maybe an active pump, such as, for example, a peristaltic-type pump, and the medicament in medicament-receiving portion is in fluid communication with the peristaltic pump conduit so that medicament is drawn from medicament-receiving portion 26 and subsequently delivered to the target site by way of the conduit. In this embodiment of U.S. Patent Application No. 2007/0106280, portion 28 may contain no propellant at all or a relatively small amount of propellant.

Regardless, in either case, the bellows mechanism of U.S. Patent Application No. 2007/0106280 includes an intermediate plate 30 disposed within the medicament-receiving portion 26. Intermediate plate 30 has at least one through-hole 32 therein to permit medicament to pass there-through. In a preferred exemplary embodiment of U.S. Patent Application No. 2007/0106280, intermediate plate 30 has four symmetrical through-holes 32. Those skilled in the art will readily appreciate that numerous other configurations can be used for intermediate plate 30 so long as they have the functionality to practice the specific embodiment. For example, plate 30 could be in the form of a grid. Plate 30 is preferably made of a biocompatible, non-magnetic material, such as, for example, titanium. According to U.S. Patent Application No. 2007/0106280, plate 30 could also be made of a combination of materials, such as, for example, a sandwich or layers of different materials, with the outer layer being biocompatible. U.S. Patent Application No. 2007/0106280 also discloses that intermediate plate 30 is preferably positioned 25% to 50% of the distance from the base plate 14 to the bottom plate 24 of bellow mechanism 20 at free length (e.g., when the bellows is in a stable state during its manufacturing). More preferably, intermediate plate 30 is disposed 33% to 40% of the distance from the base plate 14 to the bottom plate 24 of bellow mechanism 20. In a currently preferred exemplary embodiment, intermediate plate 30 is disposed approximately 40% of the distance from the base plate 14 to the bottom plate 24 of bellow mechanism 20. Thus, referring now to FIG. 1, the distance b divided by distance a (i.e., ratio b/a) is preferably 0.40, or 40%.

U.S. Patent Application No. 2007/0106280 further discloses that a coil 34 is disposed in a recess 36 on the lower surface 38 of base plate 14. A mu-metal 40 is disposed between coil 34 and base plate 14. Mu metals are nickel and iron alloys (usually 75% nickel, 15% iron and include copper and molybdenum) that offer very high magnetic permeability. This mu-metal 40 acts as a rear shield of the coil to limit the eddy current in the base plate 14. In addition, coil 34 is spaced from the internal wall, which is preferably made of titanium, by a distance. Coil 34 is isolated from the medicament chamber with a biocompatible titanium ring 35.

In a currently preferred exemplary embodiment of U.S. Patent Application No. 2007/0106280, the pump housing 12 is made of titanium. In addition, as stated above, intermediate plate 30 is also preferably made of titanium. The sensitivity in detecting the intermediate plate 30 increases with increasing thickness of plate 30. However, increasing the thickness of plate 30, increases the weight of the device and decreases the internal volume of the reservoir in the pump because intermediate plate 30 is disposed within the bellows reservoir medicament-receiving portion 26. The plate may have a thickness ranging from 0.2 mm to 0.7 mm, with 0.5 mm being preferred in a currently preferred exemplary embodiment. The value of the inductance seen across coil 34 is affected by the location of the intermediate plate 30 and bottom plate 24. The resonant frequency of the circuitry in which the coil 34 is placed is influenced by the inductance across coil 34. The amount of fluid remaining in the reservoir is determined based upon the measurement of the resonant frequency, which is correlated to the inductance. Currently pending and commonly owned U.S. patent application Ser. No. 1/278,048, filed Mar. 30, 2006, and entitled "Methods and Devices for Monitoring Fluid of an Implantable Infusion Pump" discloses, inter alia, a manner of using a fluid level sensor to monitor the amount of fluid in a reservoir. The disclosure of pending U.S. application Ser. No. 11/278,048, as well as the disclosure of U.S. Patent Application No. 2007/0106280 are both in their entirety, hereby incorporated by reference.

It is a first object of the invention to provide a method for manufacturing the metal bellows fluid reservoir including the intermediate plate of the pump described in U.S. Patent Application No. 2007/0106280.

SUMMARY OF THE INVENTION

The formation of a bellows made up of a stack of a predetermined number of ring-convolutions and having an intermediate plate supported within said stack, according to the present invention is achieved by starting with a supply of thin metal rings, each ring having a first outer diameter defining a first outer edge and a first inner diameter, defining a first inner edge. A pair of these metal rings are positioned one on top of the other in a contiguous relation to each other and their adjacent inside edges are welded together to form a ring-convolution. This process is repeated until a sufficient number of ring-convolutions are made to eventually make the desired bellows. Before these separate ring-convolutions are fused to each other, an intermediate plate and a support ring are made. The intermediate plate is a disc of metal that is sized smaller than the inside diameter of the rings and is secured to the support ring. The support ring is then positioned between two formed ring-convolutions in contiguous relationship and the three abutting outside edges are welded to each other to form a support plate convolution. The already made ring-convolutions and the support plate convolution are then stacked in the desired order and in contiguous relationship. All not-yet welded adjacent outside edges of said ring-convolutions and said support plate convolution are then welded to form the bellows. A bottom plate is formed and welded to the outside edge of the bottommost ring-convolution and a top ring is finally welded to the uppermost convolution to complete the bellows. The top ring is meant to be welded to a base plate of an infusion pump. The method includes steps for holding the rings to be welded into a jig and thereafter moving the jig with respect to the welder, or moving the welder with respect to the jig. The welder preferably includes the use of a laser wherein the output beam of the laser may be easily moved along the held rings by appropriate optics, but the welder may also be an arc-TIG type.

BRIEF DESCRIPTION OF THE DRAWINGS

The invention can be more fully understood from the following detailed description taken in conjunction with the accompanying drawings, in which:

FIG. 3 is a perspective view of an upper ring and a lower ring being assembled together, according to the method of manufacture of the present invention;

FIG. 5 is an enlarged partial section view of a fused convolution of FIG. 4, according to the method of manufacture of the present invention, showing details of the fused inner edge of the two rings;

DETAILED DESCRIPTION OF THE PREFERRED EMBODIMENTS

Figure 2:
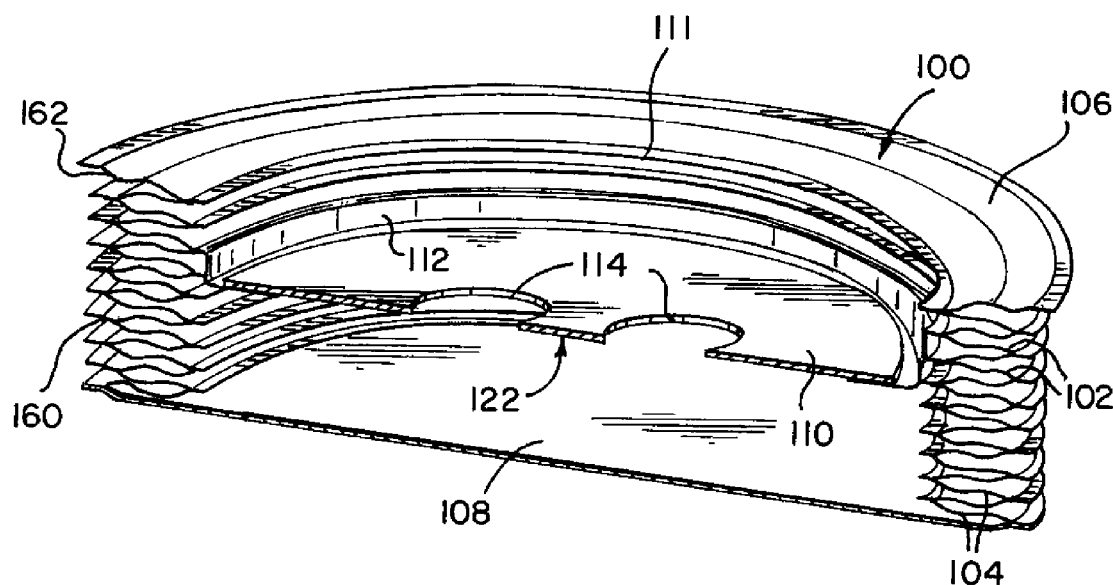
FIG. 2 is a perspective section view of the bellows of the infusion pump of FIG. 1, showing detail of upper and lower rings, an intermediate ring, an intermediate plate, a top ring and a bottom plate.
Figure 9:
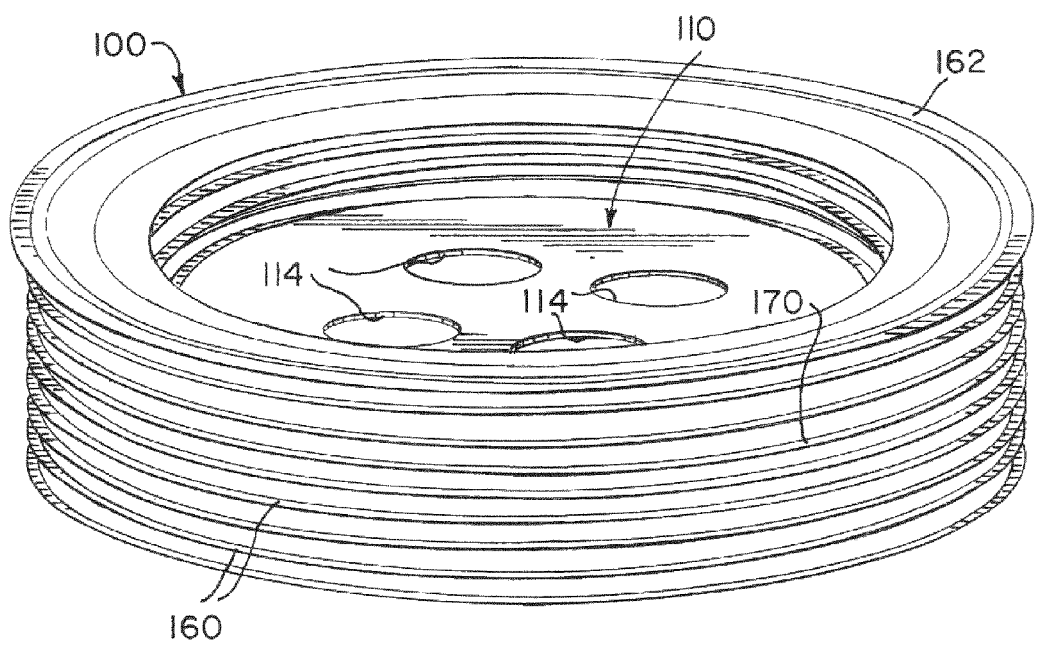
FIG. 9 is a perspective view of the fully assembled bellows made by the method of manufacture of the present invention.

Referring to FIGS. 2 and 9, a bellows 100 (cross-sectional view in FIG. 2) is shown including a plurality of upper diaphragm rings 102 (hereinafter called "upper rings") edge-welded to a plurality of lower diaphragm rings 104 (hereinafter called "lower rings", a top ring 106, a bottom plate 108, an intermediate plate 110 and an intermediate-plate support ring 112. The bellows 100 shown in FIG. 9 is manufactured primarily by welded pre-cut and formed parts together in a predetermined order, as described below.

According to the method of manufacture of the present invention, each upper and lower ring 102, 104, top ring 106, bottom plate 108, an intermediate plate 110 and an intermediate-plate support ring 112 is made by cutting a predetermined shape from an appropriate bio-compatible material, such as titanium, stainless steel, an appropriate composite, alloy, or a laminate made up of different metals and/or composites.

Figure 1:
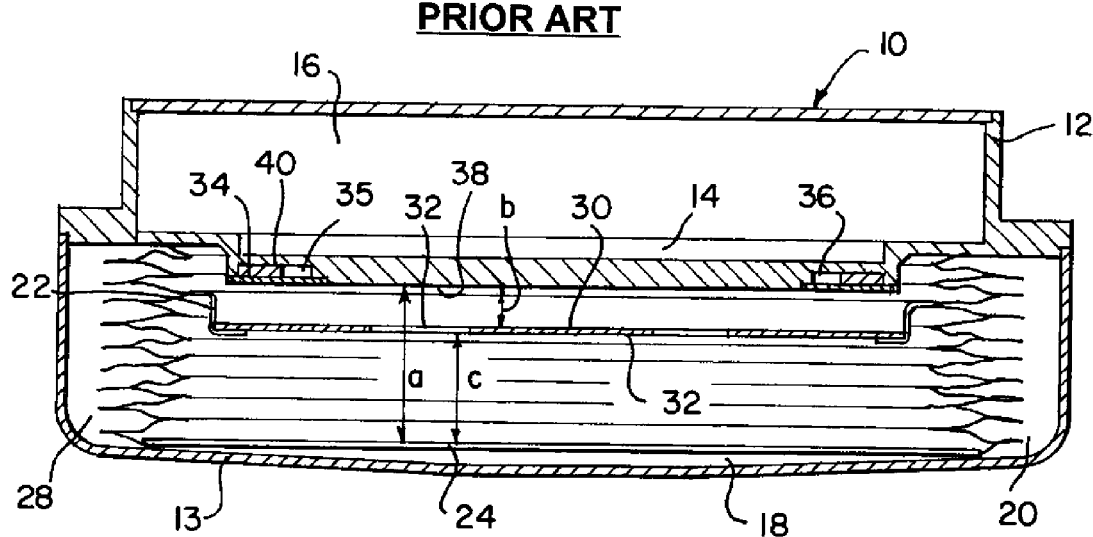
FIG. 1, labeled "Prior Art" is a cross-sectional elevation view of an infusion pump having an intermediate plate which is used to help explain the operation of the infusion pump including a metal bellows.

All the main parts of the bellows 100, including rings 102, 104, bottom plate 108, top ring 106, intermediate plate 110, and intermediate ring 112 are preferably made from titanium. The material thickness of upper and lower rings 102, 104, top ring 106 and intermediate-plate support ring 112 is within the range of 0.06 mm and 0.12 mm depending on the size and design parameters of the pump assembly, with 0.8 mm being a preferred thickness of these parts in this exemplary embodiment. The thickness of the intermediate plate 110 will also vary depending on design factors and materials selected. As mentioned above, the thicker the intermediate plate, the more accurately it will "communicate" with coil 34 (shown in FIG. 1 and described above in the background section of this application), but the heavier the pump will become and also the less volume available within the reservoir for liquid medication. In this exemplary embodiment, intermediate plate 110 is 0.5 mm thick, but may vary from 0.2 mm and 0.7 mm thick.

The basic shape of each ring 102, 104, 106, 112, bottom plate 108 and intermediate plate 110 is formed by cutting prescribed shapes from sheet titanium using any of a variety of known processes including stamping, laser-cutting, or water-jet abrasive cutting, however, a simple stamping process is preferred, owing to the speed and accuracy this well known process typically offers. The stamping machine preferable cuts the ring shape from stock sheet material in one smooth stroke, leaving clean sharp edges.

Once cut, each ring 102, 104, 106, 112, bottom plate 108 and intermediate plate 110 are formed to a desired shape using an appropriate forming process and machine, such as using a forming press.

A forming press, which is well known, employs two opposing forming dies which, in use are pressed firmly into opposing sides of an interposed metal blank to shape the blank. The dies are forced together using tremendous pressure and at times with applied heat so that the metal blank will be forced to take on the shape of the dies.

As is well known, combination machines are available that allow stamping and forming of a ring shape in one stroke. This would be preferred to simplify the manufacturing process.

The details of the cutting and forming processes are not shown in the figures of the present application since these processes are well known. The main parts of the bellows of the present invention may be made using any of a variety of processes, the specific details of which are beyond the scope of the immediate invention.

When the upper and lower rings 102, 104 are formed, each will have a distinctive concentric wave pattern of predetermined height, width and pitch formed therein. Also, upper ring 102 will have a radial slant wherein an outer edge 103 will reside within a higher plane to that of an inner edge 105. Conversely, lower ring 104 will be formed with an opposite radial slant so that an outer edge 107 will reside in a plane that is lower than that of an inner edge 109. This detail of rings 102, 104 is best shown in FIG. 3. Of course, the specific shapes of rings 102, 104 may vary according to the details of design. The rings may include several "waves" and may in some instances be formed symmetric so that an upper ring 102 is merely an inverted lower ring 104. Rings of any shape can be used with the steps of the present method without departing from the invention.

Top Ring

As described above, in this exemplary embodiment of the invention, different sets of dies would be required to form upper ring 102, lower ring 104, bottom plate 108, top ring 106 and intermediate-plate support ring 112. For example, top ring 106 is formed in a similar manner to upper and lower rings 102, 104, but is preferably larger in outside diameter and includes particular concentric pattern that allows it to be easily fused to base 14 (refer to FIG. 1 and the description above).

Intermediate Plate

Figure 6:
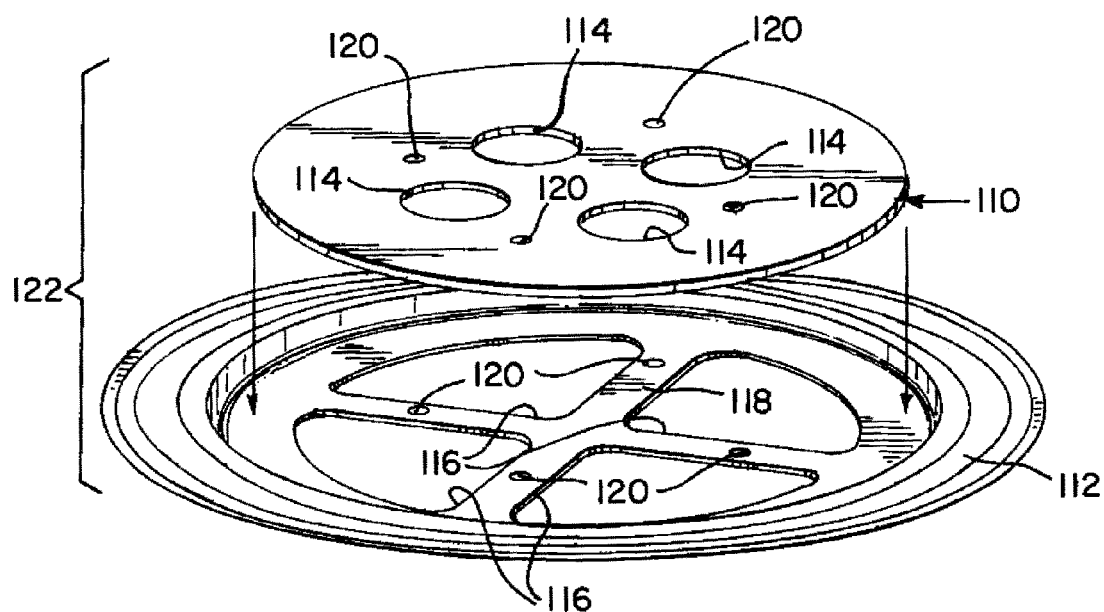
FIG. 6 is a perspective view of a schematic illustration showing the intermediate plate being fused to an intermediate-plate support ring, according to the method of manufacture of the present invention.
Figure 7:
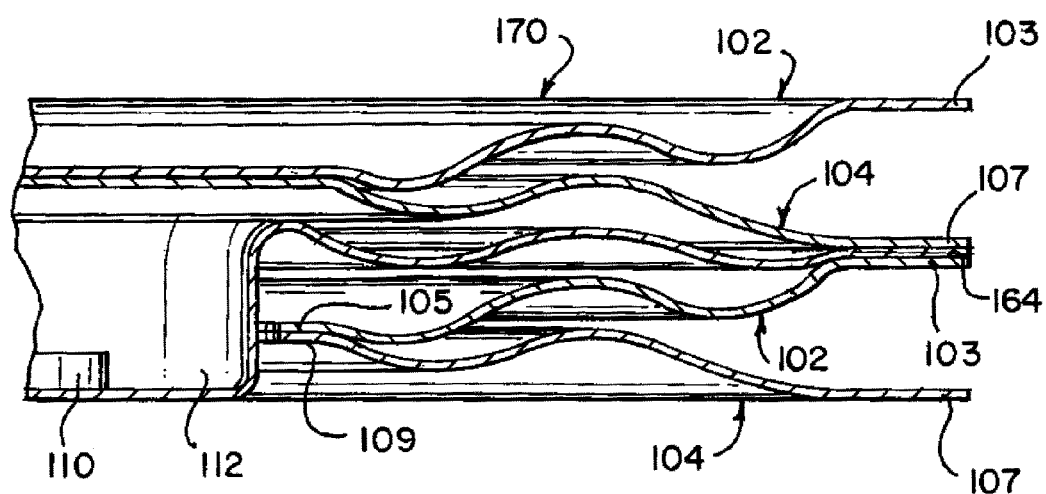
FIG. 7 is an enlarged partial section view of a fused intermediate subassembly, according to the method of manufacture of the present invention, showing details of the fused inner edges of the two convolutions and intermediate ring.

In this exemplary embodiment, intermediate plate 110 is preferably flat and requires no specific forming, however, as shown in FIGS. 2 and 6, intermediate plate 110 is preferably provided with four large openings 114, which allow liquid medication to flow freely above and below intermediate plate 110 within fluid reservoir during the operation of the pump. The large openings 114 are preferably formed by a stamping process.

Intermediate-Plate Support Ring

Also, as shown in FIGS. 2 and 6, intermediate-plate support ring 112 is formed to include a shallow dish and is thereafter stamped using a stamping machine to cut out preferably four large sections 116, as shown, to define four similarly shaped support arms 118. Each arm 118 is formed extending from the center to the outer ring, like spokes of a bicycle wheel. Support arms 118 are used to support intermediate plate 110, as described below.

As shown in FIG. 6, intermediate plate 110 is secured to support arms 118 of intermediate-plate support ring 112 using any appropriate welding technique, such as spot welding. In this exemplary embodiment, four spot welds 120 are preferably formed, one weld to each arm 118. Spot welding is a well known and commonly used technique to quickly and effectively secure two metal parts to each other using local heat transmission. The details of this process are beyond the scope of this invention and are therefore not described in any great detail. Once intermediate plate 110 is welded to intermediate-plate support ring 112, intermediate plate subassembly 122 is formed.

Figure 4:
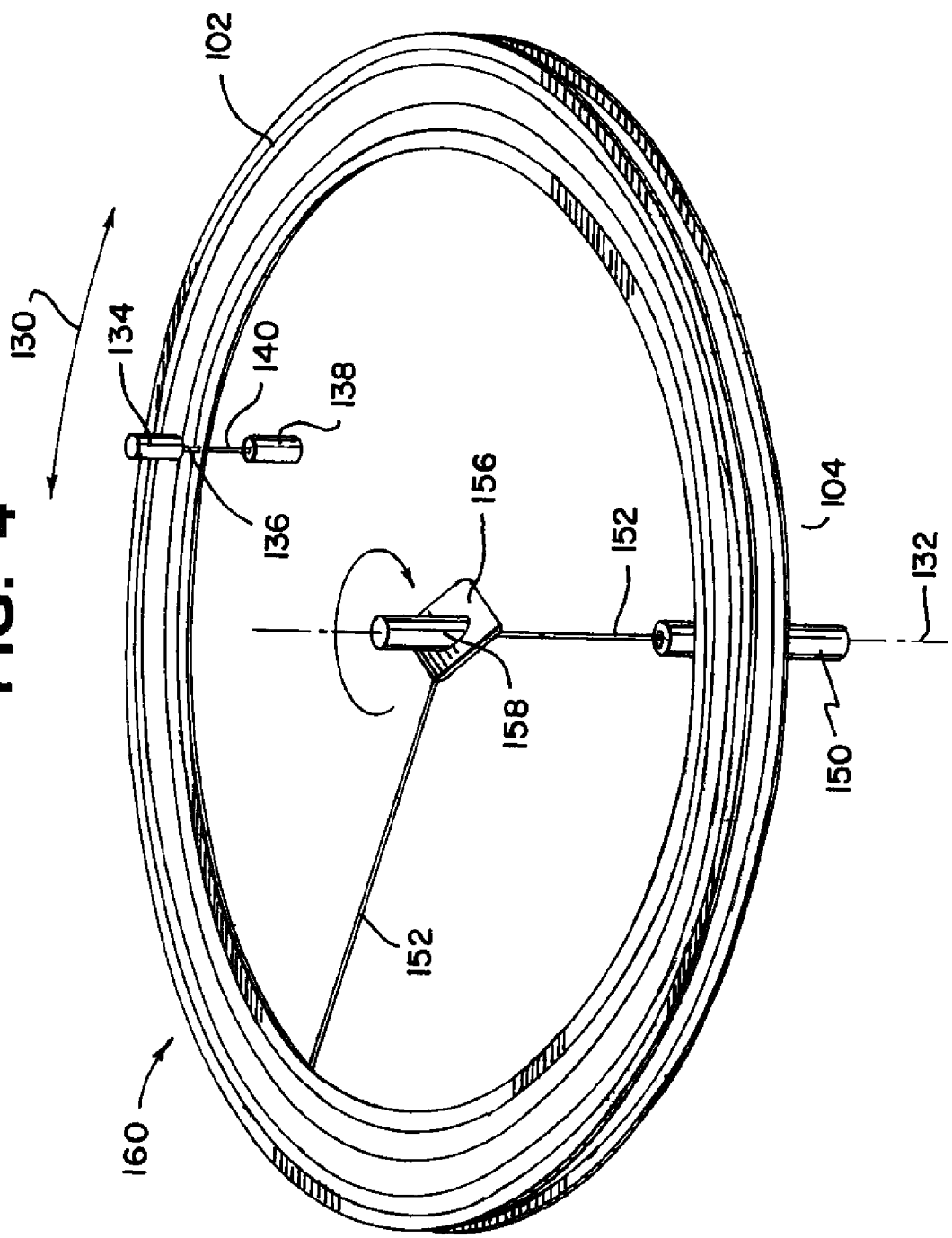
FIG. 4 is perspective view of a schematic illustration showing a welding process according to the methods of manufacture of the present invention, wherein an inner edge of an upper ring is fused to an inner edge of a lower ring, creating a "convolution"

Referring now to FIGS. 3, 4, and 5, an upper ring 102 and a lower ring 104 are secured to each other along their respective inner edges 105, 109. This is done by mounted each ring into an appropriate rotatable holding jig (not shown), which is well known in the art. The rotatable holding jig is designed to firmly hold upper ring 102 with respect to lower ring 104 so that the inner edge 105 of upper ring 102 aligns and abuts with inner edge 109 of lower ring 104. The holding jig is designed to clamp onto both rings 102, 104 in such a manner that the entire circumference of both inner edges 105, 109 of both rings are accessible to a welder and so that the inner edges are held together in an intimate contiguous relationship.

As these two rings are held by the holding jig, the jig is rotated at a controlled rotation rate and a welder is applied to effectively fuse the adjacent inner edges 105, 109 of each ring together along the entire inside circumference of the ring pair.

The conventional approach to joining such rings has been to use tungsten inert gas (TIG) to weld both the inside and outside joints. Unfortunately, TIG welding is relatively slow and may produce inconsistent quality welds. TIG welding also introduces a high level of heat energy to the metal structures which must be appropriately absorbed (using copper "chill rings") and diverted from the rings to prevent warping damage to the ring structures. To this end, a more precise and less heat-invasive laser welding process is preferably used to fuse the upper and lower rings to each other.

Referring to FIG. 4, a schematic of a laser-welder is illustrated showing an upper ring 102 secured to a lower ring 104 (jig not shown, for clarity). The two rings 102, 104 are set into a controlled rotation (represented by arrow 130) about a central axis 132. In a first laser welding arrangement, a first laser diode 134 is positioned above upper ring 102 so that an output beam 136 contacts a portion of upper ring immediately adjacent to inner edge 105. Similarly, a second laser diode 138 is positioned below lower ring 104 so that an output beam 140 contacts a portion of lower ring immediately adjacent to inner edge 109. Both beams 136 and 140 may operate together in a continuous manner or may pulse at controlled intervals and durations, as is well known in the art. The output of each laser 134, 138 is focused onto a target area preferably located immediately adjacent to the respective inner edges 105, 109 of each secured ring 102, 104.

As is well known, the focusing arrangement can be accomplished using computer controlled mirrors and lenses situated as necessary between lasers 134, 138 and the target area on the rings 102, 104 being held in the jig. Each outputs of laser 134, 138 is in the form of an energy pulse, which can be digitally shaped using appropriate optics and computer control. The pulse has sufficient energy to weld the two secured rings 102, 104 together within the target area of focus. Of course, although two lasers are shown in this example and in FIG. 4, a single laser may also be used. In such instance, the energy of the single laser pulse is controlled to be insufficient to penetrate the both rings 102, 104, but sufficient to effectively fuse the two rings together.

An infrared or other sensor can be coupled to the output optics of the laser to receive a signal indicative of the temperature achieved in the weld puddle at the top ring pair within the focus area to serve as an indicator of the weld function. A suitable feedback can be coupled to the sensor and to the laser source controls for supplying a corrective signal to the laser source.

The digital programming of the present invention may control the laser output so that an initial energy burst is followed by a rest phase. During subsequent bursts, more or less energy may be applied following a prescribed program designed for the particulars of the two rings 102, 104, until the two rings located at the target area are properly fused to each other. The pulsed bursts will produce a generally circular or elliptical spot weld. The lasers continue to spot weld the edges until the entire inside circumference has been welded. Of course, to create an effective and required hermetic seal, each spot weld will have to overlap with adjacent spot welds, as is known in the art. The locations for sequential spot welds are preferably separated sufficiently so that there is very little, if any, residual thermal energy present in the ring at the second location due to prior activity of the laser. In this way, each welded spot can be supplied with about the same amount of energy without any significant risk of delivering too much energy. The sequentially welded areas can be adjacent to each other, however such positioning can, in certain circumstances, tend to induce thermal warps in the delicate thin metal rings 102, 104.

As the holding jig rotates the ring pair with respect to the beams, 136, 140, the energy produced by the beams effectively fuses upper ring 102 to lower ring 104 along the combined respective inner edges 105, 109. The welding continues until a continuous and hermetically-tight bond is formed along the entire circumference of both upper and lower rings.

Alternatively, also shown in FIG. 4, instead of rotating the holding jig, the laser beam may be optically directed around the inner edge of both rings so that the edges are again effectively fused to each other. One way to do this is to position a laser 150 so that an output beam 152 is directed along central axis 132, perpendicular to the plane in which both rings 102, 104 contact each other, as they are both held by holding jig. A mirror 156 is attached to the shaft of a motor 158 at a 45 degree angle and positioned to capture and reflect the output beam 152 to contact the inner edges 105, 109 of both rings 102, 104. As the motor 158 rotates mirror 156, the output beam 152 of laser 150 will move along the inner edges 105, 109 and fuse them together, forming a clean weld bead. Again, as before, the output of laser 150 may be pulsed to create small spot welds that are produced in an overlapping relationship to create a hermetic seal.

To improve the quality of the resulting welds, all of the welding steps disclosed in this application are preferably performed with the working parts located either within an evacuated chamber (within a vacuum) or in the presence of an inert gas, as understood by those skilled in the art.

U.S. Patent Application 2003/0226247, filed Oct. 28, 2002 and U.S. Pat. No. 6,040,550 both disclose methods of fusing bellow rings to each other. The rings of this present application may be fused using the processes described in these two identified applications. The entirety of both U.S. Patent Application 2003/0226247 and U.S. Pat. No. 6,040,550 are hereby incorporated by reference.

Regardless how the inner edge 105 of upper ring 102 is hermetically fused to the inner edge 109 of lower ring 104, forming a "convolution" 160, the process is repeated with different upper and lower rings 102, 104, to form a sufficient number of convolutions 160 necessary to assemble the entire bellows 100. Of course the number of convolutions required will vary depending on the design of the particular bellows. A bellows that is used as a fluid reservoir within an implantable infusion pump will typically include between 6 and 12 convolutions.

Referring to FIG. 2 and using the same process described above and shown in FIG. 4, an inside edge 111 of top plate 106 is fused to an adjacent inside edge 109 of a lower ring 104 to form a top convolution 162.

According to an important aspect of the present invention, and referring to FIGS. 7, 8, 9 and 10, an outer edge 164 of intermediate plate subassembly 122 is fused to two opposing convolutions 160 at an outer edge 103, 107 of the respective upper and lower ring which make up the convolutions. As above, an appropriate holding jig (not shown) is used to hold intermediate plate subassembly 122 between two convolutions 160 so that outer edge 164 of intermediate plate subassembly 122, outer edge 103 of the lower ring 104 of one convolution 160 and outer edge 107 of upper ring 102 of the other convolution each align and abut with each other. Once the three outer edges are properly held and aligned within the holding jig, the output beam 166 of an appropriate laser 168 is directed along the combined edges so that as the holding jig rotates, all three outer edges, 164, 103, and 107 are effectively fused to each other forming a hermetic seal therealong, creating assembly 170, shown in FIG. 7 (in partial section view). As described above in connection with lasers 134, 138, the laser 168 may include appropriate optics to help guide and focus the output beam as required and may follow the same pulse programming as that described above.

Figure 8:
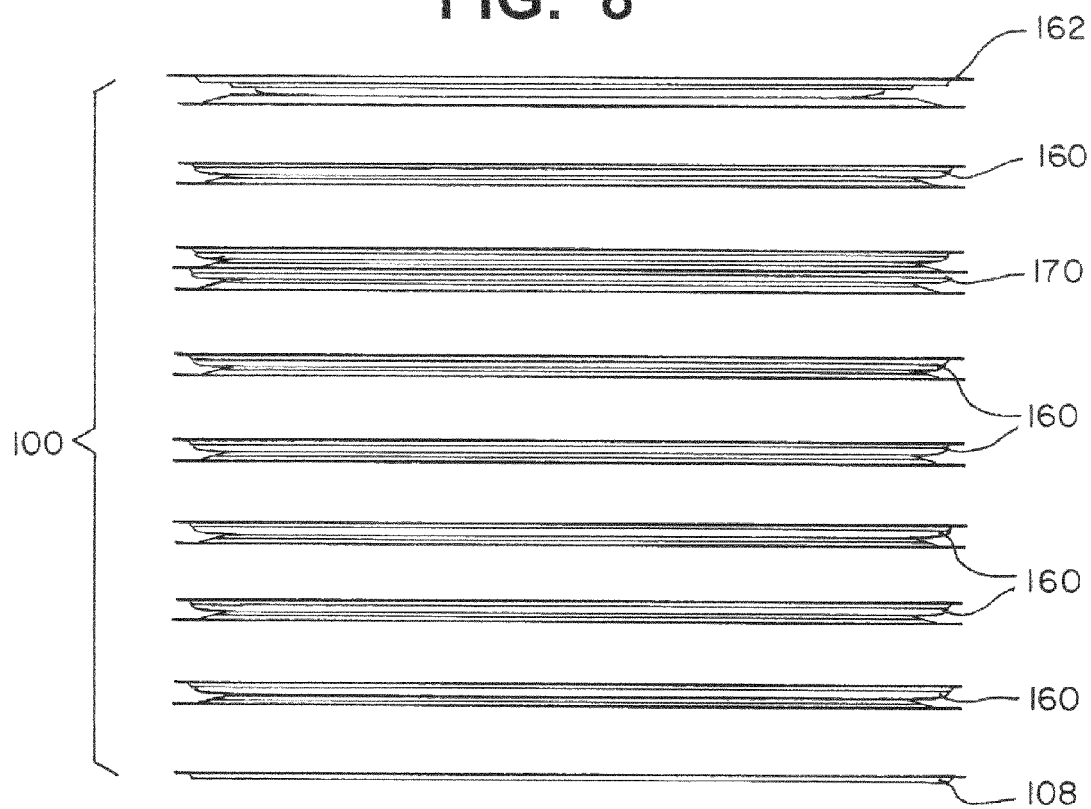
FIG. 8 is an elevation assembly view of the entire bellow assembly showing the relative positioning of each convolution and intermediate subassembly, top convolution and bottom plate, according to the method of manufacture of the present invention.

Referring now to FIG. 8, an assembly view of bellows 100 is shown to illustrate how the different parts that make up the bellows are put together in final assembly. The final assembly of this exemplary embodiment is performed using the outside-edge laser welding process described above.

To being the final assembly, top convolution 162 and a convolution 160 are positioned in an appropriate holding jig, similar to the ones described above so that top ring 106 faces away from convolution 160. Outer edge 107 of lower ring 104 of top convolution 162 is positioned into contact with outer edge 103 of upper ring 102 of convolution 160. The two outer edges are then laser welded using the outer-edge welding process described above.

Once welded together, the assembly continues by laser welding subassembly 170 (which contains intermediate plate 110 and intermediate-plate support ring 112), outer-edge to outer-edge. Next, another convolution 160 is laser welded outer-edge to outer-edge using the same process. In this exemplary embodiment, four additional convolutions 160 are laser welded, outer-edge to outer-edge. Finally, the outer edge of bottom plate 108 is laser welded to the outer edge 107 of lower rig 104 to complete the assembly.

The completed bellows 100 is shown in FIG. 9.

Figure 10:
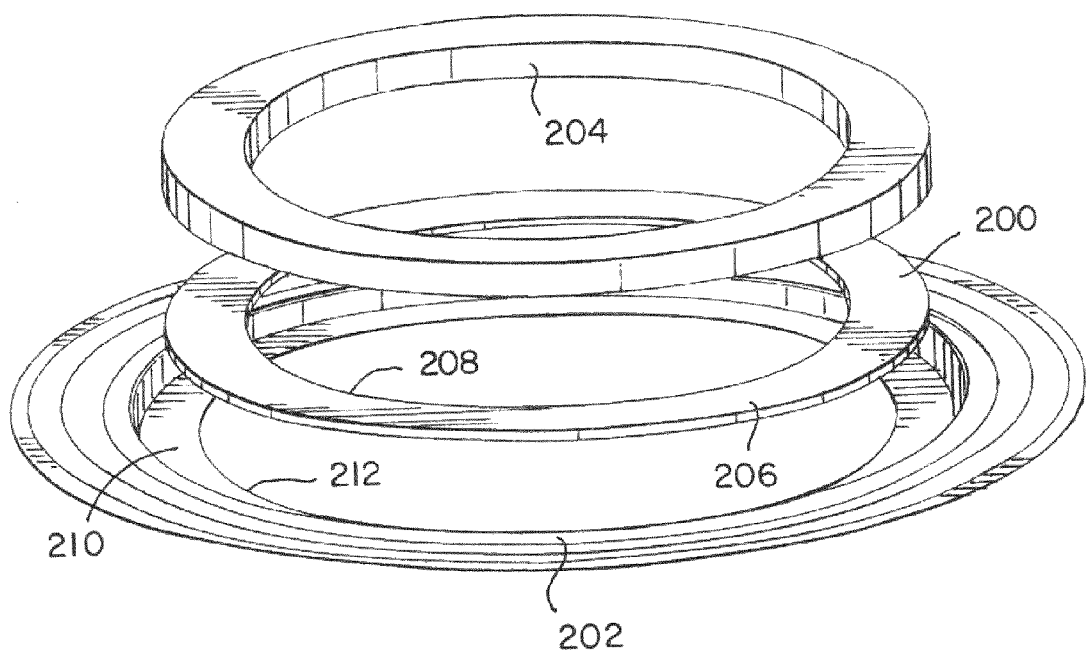
FIG. 10 is a perspective assembly view of an intermediate plate, a support ring, and a sensor coil according to a second embodiment of the invention.
Figure 11:
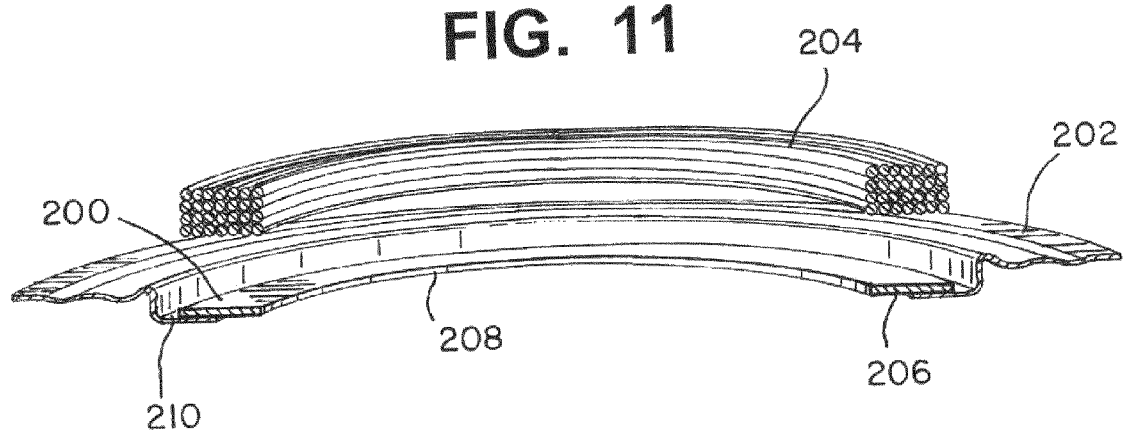
FIG. 11 is a cross-sectional perspective view of the intermediate plate, a support ring, and sensor coil of FIG. 10 shown with the intermediate plate welded to the support ring, according to the second embodiment of the invention.

Referring now to FIGS. 10 and 11, an intermediate plate 200, a support ring 202 and an exemplary sensor coil 204 are shown according to a second embodiment of the invention. Sensor coil 204 is similar to coil 34 of FIG. 1 (Prior Art) and described above in the Background of the Invention section of this application. Coil 204 is made from a coil of wire and is located within the pump assembly (not shown in FIGS. 10 and 11. Coil 204 is electrically connected to a well known sensing circuit (not shown). Coil 204 (like coil 34) essentially functions as an inductive proximity sensor and uses the inductive influence of intermediate plate 200 to determine the distance between the plate and the coil.

As can be seen in the figures, intermediate plate 200 is ring shaped having an outside diameter defining an outer edge 206 and having an inside diameter defining an inner edge 208. Support ring 202 includes a support ledge 210 which is sized and shaped to receive intermediate plate 200. Support ledge 210 defines an inner edge 212 having an inside diameter. Inside diameter of inner edge 212 is less than the outside diameter of intermediate plate 200, but greater than the inside diameter of intermediate plate 200. This will allow an overlap between support ledge 210 and intermediate plate 200. This overlap allows intermediate plate 200 to be spot welded to support ledge 210 and also support ring 202.

By being ring shaped, intermediate plate 200 offers a large central opening 214 which allows the liquid medication located within the bellows to move freely around intermediate plate 200. Ring shaped intermediate plate 200 is preferably shaped similarly to ring-shaped sensor coil 204 so that it remains effective at communicating with sensor coil 204 so that the magnitude of collapse of the bellows can be accurately sensed, as described above in the Background of the Invention section of this application. The ring shape of intermediate plate 200 according to this embodiment also allows the plate to be as light as possible so that its presence does not adversely influence the movement of the bellows.

Once the intermediate plate 200 is welded to support ring 202, support ring may be welded to the other rings which make up the bellows as described above in the method of manufacture of the present invention. Intermediate plate 200 and support ring 202 may be made using the same steps described above used to manufacture intermediate plate 110 and intermediate support plate 112 and can also be made from one of the same selection of materials, preferably titanium. Sensor coil 204 is shown in FIGS. 10 and 11 as exemplary to help explain this embodiment of the invention. Sensor coil 204 can take on other shapes. The point of this second embodiment is to minimize the size and weight of the intermediate plate 200 without effecting its communication with sensor coil 204.

In operation, a sensing circuit (not shown) including a capacitor is electrically connected to coil 204 which is disposed within the base plate of the pump (not shown). This sensing circuit is used to form a resonant circuit. When energized, coil 204 generates a primary electromagnetic field, which flows through the intermediate plate 200 and induces eddy currents therein. The strength of these eddy currents increases as the intermediate plate 200 plate moves closer to coil 204. As is well known, the eddy currents generate a secondary magnetic field, which is coupled back to the primary field. The closer intermediate plate 200 is to coil 204, the stronger the secondary magnetic field is and its influence on the primary field. This flux coupling brings about change to the inductance of coil 204 and thus brings about a displacement or shift of the resonance frequency of the resonant circuit depending on the distance between the coil and intermediate plate 200. Upon measuring the resonance frequency, which is dependent upon the inductance, well known circuitry can be employed to calculate the distance that the intermediate plate of the bellows mechanism is from the base plate. This distance can then be used to determine the effective volume of the fluid reservoir and also the amount of medicament remaining within the bellow mechanism. An appropriate circuit can use this information to selectively create an alarm signal in response to a predetermined resonant frequency being reached.

It will be understood that the foregoing is only illustrative of the principles of the invention, and that various modifications can be made by those skilled in the art without departing from the true spirit and scope of the invention as defined by the appended claims. For example, the above described steps illustrate the method of manufacturing an exemplary metal bellows 100, according to the invention, wherein intermediate plate 110 is positioned between the second and third convolution 160 from top ring 106 and further includes five additional convolutions 160 between bottom plate 108 and intermediate plate 110. Other arrangements can similarly be assembled without departing from the invention.

What is claimed is:

1. A method for forming a bellows made up of a stack of a predetermined number of ring-convolutions and having an intermediate plate supported within said stack, said method comprising the steps of:
   a) supplying a plurality of metal rings, each ring having a first outer diameter defining a first outer edge and a first inner diameter, defining a first inner edge;
   b) positioning a pair of said metal rings in contiguous relation to each other,
   c) welding said first inner edges of said pair of metal rings to each other to form a ring-convolution;
   d) repeating steps (a) through (c) until said predetermined number of ring-convolutions are made;
   e) supplying a support ring, said support ring having a second outer diameter that is equal to said first outer diameter of said metal rings and adapted to hold an intermediate plate;
   f) supplying said intermediate plate having a predetermined thickness and a third inside diameter that is less than said first inside diameter of said metal rings;
   g) welding said intermediate plate to said support ring;
   h) positioning said support ring between a pair of ring-convolutions in contiguous relation to each other;
   i) welding said second outer edge of said support ring to said first outer edges of said respective adjacent ring-convolutions to form a support plate convolution;
   j) positioning said ring-convolutions of (c) and said support plate convolution of step (i) in a prescribed stacked order in contiguous relation to each other; and
   k) welding all not-yet welded adjacent outside edges of said ring-convolutions and said support plate convolution to form said bellows.

2. The method of claim 1, wherein the welding steps (c), (i), and (k), are performed using a laser producing a high-energy output beam.

3. The method of claim 2, wherein the welding steps are performed by:
   holding said rings to be welded in a jig; and
   moving said output beam of said laser with respect to said held rings so that the output beam contacts the rings and fuses them together at the point of contact.

4. The method of claim 2, wherein the welding steps are performed by:
   holding said rings to be welded in a rotatable jig; and
   rotating said jig with respect to said output beam of said laser so that the output beam contacts the rings and fuses them together at the point of contact.

5. The method of claim 2, wherein said laser pulses said output beam so that the resulting weld is formed by multiple small spot welds.

6. The method of claim 5, wherein adjacent spot welds overlap each other by a predetermined amount.

7. The method of claim 6, wherein said overlap is between 30% and 75%, measured in area.

8. The method of claim 1, wherein the welding steps (c), (i), and (k) are performed using a TIG (Tungsten Inert Gas) welder.

9. The method of claim 8, wherein the welding steps are performed by:
   holding said rings to be welded in a jig; and
   moving said TIG welder with respect to said held rings so that the heat energy of the TIG welder contacts the rings and fuses them together at the point of contact.

10. The method of claim 8, wherein the welding steps are performed by:
    holding said rings to be welded in a rotatable jig; and
    rotating said jig with respect to said TIG welder so that the TIG welder contacts the rings and fuses them together at the point of contact.

11. The method of claim 1, wherein said welding step (g) is performed using a electrical-current spot welder.

12. The method of claim 1, wherein said rings and support plate are made from titanium metal.

13. The method of claim 1, wherein said steps further include:
    providing a bottom cover having an outer diameter which is equal to said first outer diameter of a ring;
    positioning said bottom cover and said bottom ring-convolution of said stack in contiguous relationship, and
    welding said adjacent outer edges of said ring-convolution and said bottom ring.

14. The method of claim 13, wherein said bellows stack is further attached to a base plate of an implantable infusion pump and used as a fluid reservoir to hold a supply of liquid medication.

15. The method of claim 14, wherein an attached step includes laser welding.

16. A method for forming a bellows made up of a stack of a predetermined number of ring-convolutions and having an intermediate plate supported within said stack, said method comprising the steps of:
    a) supplying a plurality of metal rings, each ring having a first outer diameter defining a first outer edge and a first inner diameter, defining a first inner edge;
    b) positioning a pair of said metal rings in contiguous relation to each other,
    c) welding said first inner edges of said pair of metal rings to each other to form a ring-convolution;

d) repeating steps (a) through (c) until said predetermined number of ring-convolutions are made;
e) supplying a support ring, said support ring having a second outer diameter that is equal to said first outer diameter of said metal rings and adapted to hold said intermediate plate;
f) supplying an intermediate plate having a predetermined thickness and a third inside diameter that is less than said first inside diameter of said metal rings;
g) welding said intermediate plate to said support ring;
h) positioning said support ring between a pair of ring-convolutions in contiguous relation to each other;
i) welding said second outer edge of said support ring to said first outer edges of said respective adjacent ring-convolutions to form a support plate convolution;
j) positioning a pair of ring-convolutions of (c) in contiguous relation to each other;
k) welding said abutting outside edges of said pair of ring-convolutions to each other, forming a stack of connected convolutions;
l) positioning another ring-convolution to said stack of step (k), again in contiguous relation;
m) welding said outside edge of said added ring-convolution to said adjacent outside edge of an adjacent ring-convolution of said stack;
n) repeating steps (l) and (m), until said stack reaches a predetermined location of said support convolution within said stack;
o) positioning said support convolution onto said stack in contiguous relation; and
p) welding said adjacent outside edges of said added support convolution with said adjacent outside edge of an adjacent ring-convolution of said stack to complete said bellows.

17. The method of claim 16, wherein the welding steps (c), (i), (k), (m), and (p) are performed using a laser producing a high-energy output beam.

18. The method of claim 17, wherein the welding steps are performed by:
holding said rings to be welded in a jig; and
moving said output beam of said laser with respect to said held rings so that the output beam contacts the rings and fuses them together at the point of contact.

19. The method of claim 17, wherein the welding steps are performed by:
holding said rings to be welded in a rotatable jig; and
rotating said jig with respect to said output beam of said laser so that the output beam contacts the rings and fuses them together at the point of contact.

20. The method of claim 17, wherein said laser pulses said output beam so that the resulting weld is formed by multiple small spot welds.

21. The method of claim 20, wherein adjacent spot welds overlap each other by a predetermined amount.

22. The method of claim 21, wherein said overlap is between 30% and 75%, measured in area.

23. The method of claim 16, wherein the welding steps (c), (i), (k), (m), and (p) are performed using a TIG (Tungsten Inert Gas) welder.

24. The method of claim 23, wherein the welding steps are performed by:
holding said rings to be welded in a jig; and
moving said TIG welder with respect to said held rings so that the heat energy of the TIG welder contacts the rings and fuses them together at the point of contact.

25. The method of claim 23, wherein the welding steps are performed by:
holding said rings to be welded in a rotatable jig; and
rotating said jig with respect to said TIG welder so that the TIG welder contacts the rings and fuses them together at the point of contact.

26. The method of claim 16, wherein said welding step (g) is performed using a electrical-current spot welder.

27. The method of claim 16, wherein said rings and support plate are made from titanium metal.

28. The method of claim 16, wherein said steps further include:
providing a bottom cover having an outer diameter which is equal to said first outer diameter of a ring;
positioning said bottom cover and said bottom ring-convolution of said stack in contiguous relationship, and
welding said adjacent outer edges of said ring-convolution and said bottom ring.

29. The method of claim 28, wherein said bellows stack is further attached to a base plate of an implantable infusion pump and used as a fluid reservoir to hold a supply of liquid medication.

30. The method of claim 29, wherein an attached step includes laser welding.

31. The method of claim 1, wherein the first outside diameter of all of the metal rings is the same.

32. The method of claim 1, wherein the first inside diameter of all of the metal rings is the same.

33. The method of claim 31, wherein the first inside diameter of all of the metal rings is the same.

34. The method of claim 16, wherein the first outside diameter of all of the metal rings is the same.

35. The method of claim 16, wherein the first inside diameter of all of the metal rings is the same.

36. The method of claim 34, wherein the first inside diameter of all of the metal rings is the same.

* * * * *